United States Patent [19]

Saito et al.

[11] 4,280,951
[45] Jul. 28, 1981

[54] FLAME RETARDANTS

[75] Inventors: Toranosuke Saito, Kobe; Hiroyuki Ohishi, Moriyama, both of Japan

[73] Assignee: Sanko Kaihatsu Kagaku Kenkyusho, Osaka, Japan

[21] Appl. No.: 162,007

[22] Filed: Jun. 23, 1980

Related U.S. Application Data

[63] Continuation-in-part of Ser. No. 39,769, May 17, 1979, abandoned.

[30] Foreign Application Priority Data

May 24, 1978 [JP] Japan .................................. 53-61047

[51] Int. Cl.³ .......................... C08K 5/53; C07F 9/32
[52] U.S. Cl. .......................... 260/45.8 R; 260/927 R; 260/936; 260/961; 260/982; 528/72; 528/108; 528/287; 525/340
[58] Field of Search ............. 260/45.8 R, 927 R, 936, 260/961, 982; 528/72, 108, 287

[56] References Cited

U.S. PATENT DOCUMENTS

| | | | |
|---|---|---|---|
| 3,468,983 | 9/1969 | Praetzel et al. | 260/953 |
| 3,480,594 | 11/1969 | Price | 260/2.5 |
| 3,702,878 | 11/1972 | Saito | 260/45.8 R |
| 3,897,398 | 7/1975 | Beninate et al. | 260/77.5 AQ |
| 3,919,170 | 11/1975 | Allard | 260/47 CB |
| 4,035,343 | 7/1977 | Bollert | 260/75 P |
| 4,086,206 | 4/1978 | Saito et al. | 525/434 |
| 4,113,795 | 9/1978 | Izawa et al. | 525/391 |
| 4,137,201 | 1/1979 | Kuo et al. | 260/45.8 R |
| 4,157,436 | 6/1979 | Endo et al. | 528/287 |
| 4,185,006 | 1/1980 | Rasberger et al. | 260/927 R |

FOREIGN PATENT DOCUMENTS

| | | |
|---|---|---|
| 2034887 | 10/1975 | Fed. Rep. of Germany |
| 50-17979 | 6/1975 | Japan |
| 1256180 | 12/1971 | United Kingdom |

*Primary Examiner*—V. P. Hoke
*Attorney, Agent, or Firm*—McAulay, Fields, Fisher, Goldstein & Nissen

[57] ABSTRACT

Phosphorus-containing condensation products are obtained by effecting condensation between an organophosphorus compound of the Formula,

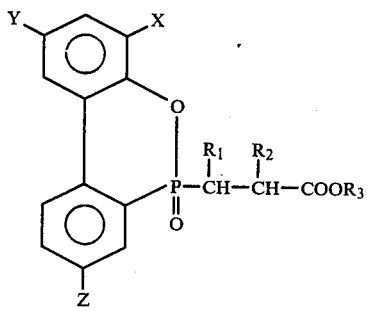

wherein X, Y and Z each is hydrogen or halogen, $R_1$ and $R_2$ each is hydrogen or methyl and $R_3$ is hydrogen or an alkyl group and polyhydric alcohols having at least three alcoholic hydroxyl groups.

These condensation products are useful as a flame retardant for various synthetic resins.

6 Claims, No Drawings

FLAME RETARDANTS

CROSS REFERENCE TO RELATED APPLICATIONS

This application is a continuation-in-part of our copending application Ser. No. 039,769, now abandoned, filed May 17, 1979 for "Flame Retardants."

BACKGROUND OF THE INVENTION

This invention relates to a flame retardant comprising phosphorus-containing condensation products.

Organophosphorus or organohalogen compounds have been used as a flame retardant for synthetic resins as disclosed in, for example, U.S. Pat. Nos. 3,247,134, 3,262,894, 3,278,464, 3,359,220, 3,368,916 and 3,372,141; British Pat. Nos. 1,015,212, 1,094,723, 1,108,064; and Belgian Pat. No. 709,417. However, when the conventional organophosphorus compounds are added to resins in an amount sufficient to impart flame retardancy, there are disadvantages that properties of the resin, such as heat resistance and impact strength are reduced.

SUMMARY OF THE INVENTION

An object of this invention is to provide a flame retardant exhibiting a flame-retarding effect on synthetic resins without lowering properties thereof.

Another object of this invention is to provide a flame retardant resin composition containing phosphorus-containing condensation products.

In accordance with this invention, there is provided a flame retardant comprising phosphorus-containing condensation products of an organophosphorus compound represented by Formula I,

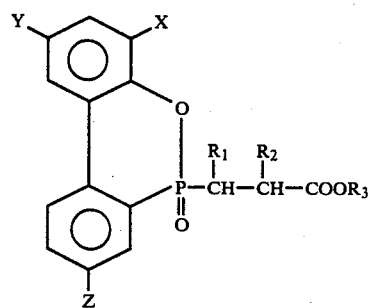

wherein X, Y and Z each is hydrogen or halogen, $R_1$ and $R_2$ each is hydrogen or methyl and $R_3$ is hydrogen or an alkyl group with a polyhydric alcohol having at least three alcoholic hydroxyl groups.

DETAILED DESCRIPTION OF THE INVENTION

Organophosphorus compounds of Formula I may be prepared by heating-adding an organophosphorus compound of Formula II,

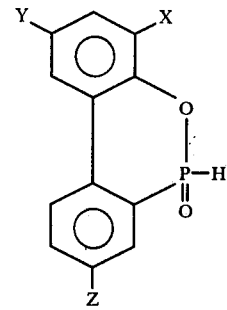

wherein X, Y and Z are as defined above to an unsaturated compound of Formula III,

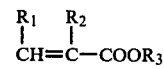

wherein $R_1$, $R_2$ and $R_3$ are as defined above.

Compounds of the Formula II which may be used in this invention are known and may be prepared by the method disclosed in U.S. Pat. No. 3,702,878 or Japanese Patent Publication No. 17979/75 or methods similar thereto.

For example, compounds of Formula IV,

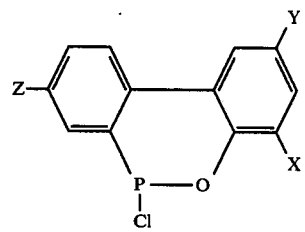

wherein X, Y and Z are as defined above are obtained by reaction of 1 mole of a substituted o-phenylphenol compound of Formula V,

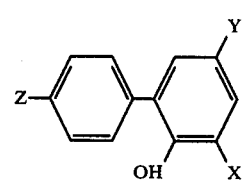

wherein X, Y and Z are as defined with 1.3 moles of phosphorus trichloride in the presence of 0.003 moles of zinc chloride at temperatures of 130° to 200° C. for about 20 hours. The compound of the Formula IV thus obtained is purified by distillation and hydrolyzed by adding an excess of water and, then, the remaining water is removed under the reduced pressure of about 10 mm Hg thereby to form compounds of Formula II.

Typical examples of compounds of Formula II include 9,10-dihydro-9-oxa-10-phosphorphenanthrene-10-oxide; 6,8-dichloro-9,10-dihydro-9-oxa-10-phosphorphenanthrene-10-oxide; 2,6,8-trichloro-9, 10-dihydro-9-oxa-10-phosphorphenanthrene-10-oxide; 6-bromo-9,10-dihydro-9-oxa-10-phosphorphenanthrene-10-oxide; 6,8-dibromo-9, 10-dihydro-B 9-oxa,-10-phosphorphenanthrene-10-oxide; and 2,6,8-tribromo-9, 10-dihydro-9-oxa-10-phosphorphenanthrene-10-oxide.

Examples of compounds of Formula III are acrylic acid, methacrylic acid, crotonic acid and alkyl esters thereof, such as methyl acrylate, ethylacrylate, butyl acrylate, octyl acrylate, methyl methacrylate, ethyl methacrylate, propyl methacrylate, butyl methacrylate, octyl methacrylate, methyl crotonate, ethyl crotonate, butyl crotonate and octyl crotonate.

These compounds are subjected to an addition reaction with compounds of Formula II to form compounds of Formula I.

The addition reaction is effected quantitatively in general and the progress of reaction is confirmed by disappearane of the P-H bond according to the infrared absorption spectrum. Since acrylic acid, methacrylic acid and esters thereof are polymerizable, in some cases polymerization reaction takes place simultaneously with the addition reaction. For avoiding the polymerization, it is preferred that these are added dropwise slowly to the compound of Formula II as the reaction advances. Further, the polymerization reaction can be perfectly prevented by adding a small amount of polymerization inhibitor to the reaction system.

The addition reaction may be effected in the absence of catalysts or in the presence of alkaline catalysts at temperatures of 50°-180° C. for 2-10 hours. The unsaturated compound of Formula III is removed from the reaction products under vacuum or, if desired, the reaction products are purified by a solvent recrystallization method. The compound of Formula I thus obtained is subjected to condensation reaction with polyhydric alcohols having at least three alcoholic hydroxyl groups to obtain a flame retardant condensation product.

Alternatively, flame retardants may be produced by effecting an addition reaction between acrylic, methacrylic or crotonic acid esters of polyhydric alcohol having at least three alcoholic hydroxyl groups and compounds of Formula II. The product obtained by this process cannot be distinguished from the condensation product obtained by the foregoing process.

The polyhydric alcohols which can be employed according to the present invention are those having at least three alcoholic hydroxyl groups and are selected from the class consisting of glycerine, polyglycerines, trimethylol ethane, trimethylol propane, pentaerythritol, dipentaerythritol, tripentaerythritol, tetrapentaerythritol, mannite, and sorbite. The polyhydric alcohols, as will be observed, do not contain hetero atoms.

Polyhydric alcohols which have good heat resistance are particularly suitable for the purpose of this invention. They include pentaerythritol and its polycondensates, such as dipentaerythritol, tripentaerythritol, and tetrapentaerythritol. Polycondensates of pentaerythritol are formed by dehydrocondensation of pentaerythritol or dipentaerythritol. When compounds of Formula I are subjected to a heat condensation with pentaerythritol or dipentaerythritol, it is observed that the polycondensation reaction of pentaerythritol units occurs simultaneously. There is effected the condensation reaction between polyhydric alcohols and compounds of Formula I corresponding to the number of alcoholic hydroxyl groups involved in the former.

In the case of monohydric alcohols or dihydric alcohols, the number of compounds of Formula I capable of reacting is only one or two. Accordingly, the condensation products thus derived are reduced in heat resistance and impact strength, so that the purposes of the present invention cannot be attained.

The condensation reaction is, in general, effected at temperatures of 100° C.-300° C., preferably 150°-250° C. It may be accelerated in the presence of a catalyst, such as, for example, sulphuric acid, phosphoric acid, benezenesulfonic acid or paratoluenesulfonic acid, sodium hydroxide, potassium hydroxide, sodium methylate, sodium ethylate, or metal compounds such as zinc acetate, lead acetate, antimony oxide or germanium oxide. For the purpose of removing completely water or alcohols which are formed during the condensation reaction, it is desirable that the reaction system is placed under vacuum at the end of reaction. Compounds of Formula I may be reacted with polyhydric alcohols in any ratio relative to the number of hydroxyl groups thereof.

When the amount of unreacted material of Formula I remaining in the condensation product is too large, the physical properties of the flame retardant resin composition are produced. Thus, it is preferred that there be less than 30 excess parts of unreacted Formula I compound for each 100 reacted parts of that compound. When the amount of unreacted Formula I compound is too large, the heat resistance and impact strength, which are the properties of a flame retardant composition of this invention, are reduced. When the number of the Formula I compound to be reacted is less than the number of hydroxyl groups, unreacted hydroxyl groups remain in the reaction product. The remaining hydroxyl groups have significant influence on the properties of a flame retardant.

When the condensates just described have an excess of unreacted hydroxyl groups, they serve as a reactant when incorporated with thermosetting resins. On the other hand, when there is an excess of Formula I compound, based upon the condensation reaction, there is no reaction with thermosetting resins.

Thus, the condensates of the present invention are not necessarily reacted, even with thermosetting resins. The question of reaction of the condensates, even with thermosetting resins, is not the essence of the present invention. The flame retardancy of the material of the present invention is substantially unaffected by reaction, or lack of reaction.

In a flame retardant of this invention, since controlling a hydroxyl value of condensation products is easy, it is possible to produce a flame retardant having a hydroxyl value suitable for each of the resin substrates. As polyurethane resins, epoxy resins and phenolic or amino resins are reactive with such hydroxyl groups, flame retardants having hydroxyl groups are bonded chemically with the resin substrate so that the lowering of properties of the resin composition obtained is small. It is, thus, preferred that hydroxyl groups are allowed to remain in the condensation product.

On the other hand, when the number of the remaining hydroxyl groups is too large, the ratio of polyhydric alcohols which have not been reacted with compounds of Formula I is increased. It is, therefore, preferred that the number of hydroxyl groups reacted with the Formula I compound is more than 35 relative to 100 of number of hydroxyl groups in the polyhydric alcohol used for reaction. It is, thus, desirable to effect the reaction in such a manner that the number of hydroxyl groups of the Formula I compound is within the range of 35 to 130, preferably 50 to 110 relative to 100 of the number of hydroxyl groups in the polyhydric alcohol.

The condensation reaction may be advanced to the degree of at least 90% relative to the theoretical ester condensation ratio which is obtained from the ratio of compounds of Formula I to polyhydric alcohols. Condensation products thus obtained have a phosphorus content of 6.0–10.7% by weight and a softening point of 55°–155° C. The high phosphorus content and softening point are characteristics of a flame retardant of this invention.

Condensation products having a hydroxyl value of less than 30 exhibit good miscibility or compatibility with, particularly, polystyrenes, acrylonitrile-styrene resins, acrylonitrile-butadiene-styrene resins, polyvinyl chloride, polyterephthalate resins, polycarbonate resins, polyphenylene oxide resins and unsaturated polyester resins. Condensation products having a hydroxyl value of more than 50 exhibit good miscibility or reactivity with polyamide resins, polyurethane resins, epoxy resins and phenolic or amino resins.

Flame retardants of this invention can be applied to various resins. Thermoplastic resins which may be used include styrene polymers and styrene graft polymrs, such as polystyrene, acrylonitrile-styrene compolymers, acrylonitrile-butadiene-styrene copolymers, vinyl chloride polymers and vinyl chloride-vinyl acetate copolymers, polyterephthalate resins such as polyethyleneterephthalate, polybutyreneterephthalate, polycondensates and copolycondensates of phthalic acid with dihydric phenols, polycarbonate resins such as polycondensates and copolycondensates of carbonic acid with dihydric phenols, polyamide resins such as 6-Nylon and 6,6-Nylon, and polyphenylene oxide resins such as oxidized polycondensates of 2,6-xylenol, mixtures thereof with polystyrene and graft polymers thereof with styrene. Thermosetting resins which may be used include polyurethane resins, addition products of polyhydroxy compounds with polyisocyanate, epoxy resins consisting of oxirane ring compounds and curing agents, phenolic resins including polycondensates of phenol or substituted phenols with formaldehyde and modified products thereof, amino resins including urea-formaldehyde resins, urea-melamine-formaldehyde resins, melamine-formaldehyde resins and melamine-benzoguanamine-formaldehyde resins and unsaturated polyester resins including copolymers of maleic acid esters and styrene and copolymers of allyl esters and acrylic esters.

For obtaining homogeneous resin compositions it is desirable to blend condensation products of this invention with thermoplastic resins while melting. For polyurethane resins the flame retardant is dissolved in polyhydroxy compounds which are then mixed and reacted with polyisocyanates. Flame retardants in which hydroxyl groups remain are reactive with polyisocyanates and thus involved in polymeric chains of the resin. For epoxy resins flame retardants may be mixed preliminarily either with oxirane ring compounds or curing agents. As for phenolic resins it is possible to mix the resin with the flame retardant and optionally curing agents, in the form of powders, and then mold under heating.

Amino resins may be blended, similarly, in form of powders and then subjected to a heat molding or when amino resins are in form of an aqueous solution or a suspension in water, flame retardants which have been milled to fine powders are suspended therein and the heat curing is effected. It is noticed that flame retardants in which hydroxyl groups remain are chemically bonded with amino resins during the curing. In case of a two-part type unsaturated polyester flame retardants may be dissolved in any one of the two liquids or both prior to curing.

When the flame retardant condensates of the present invention include an excess of unreacted OH groups, and these are incorporated with thermosetting resins, there is an extremely small diminishment in the properties of the resin composition. Further, the flame retardant condensates of the present invention are not necessarily reacted, even with thermosetting resins, but, rather, may be supported within the resin body. Thus, the flame retardant condensates of the present invention can be combined with the thermosetting resins in two different ways.

The amount of flame retardants to be incorporated in resin compositions will vary depending on the degree of flame retardancy, the type of resin and the structure of flame retardant. In general, flame retardants are added within the range of 3 to 50 parts by weight based on 100 parts by weight of resin. The flame retardants which are added are, of course, those having the phosphorous content of from 6 to 10.7%, by weight, as previously disclosed.

This invention will be illustrated by the following non-limitative examples. A softening point is herein measured by a capillary tube method.

EXAMPLE 1

648 g (3 moles) of 9,10-dihydro-9-oxa-10-phosphorphenanthrene-10-oxide are charged into a four-necked flask of 1,000 ml in capacity provided with a thermometer, a dropping funnel, a reflux condenser and a stirrer. Heating the flask, the contents melt completely at 130° C. and then stirring is effected. After elevating to 150° C., 216 g (3 moles) of acrylic acid are added dropwise from the dropping funnel at this temperature over 3 hours. Thereafter the temperature of the contents is elevated and maintained at 180° C. for 3 hours. The reaction products are poured into a stainless vat and solidified to glass. The glassy product is purified by recrystallization in dioxane to obtain white crystalline powders.

It is confirmed that the product obtained has the following structure.

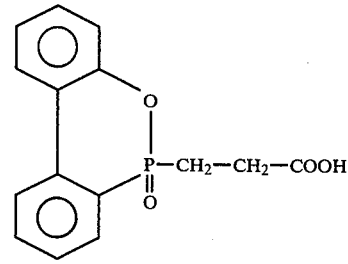

Melting Point: 130° C.
Acid Value: 196 (Calculated 194.4)
Phosphorus Content: 10.6% (Calculated 10.76%)

EXAMPLE 1-2

432 g (1.5 moles) of the product of Example 1 and 55.2 g (1.5 × 7/8 × 1.2 moles) of glycerine are charged into a four-necked flask of 500 ml in capacity provided with a thermometer, a gas inlet, a water outlet and a stirrer. Heating the flask, the contents melt at 140° C. and then stirring is effected. When the temperature is elevated at a rate of 20° C. per one hour under stirring, condensation reaction advances while forming water. After elevating the temperature to 220° C., the water outlet is connected with a vacuum pump and this temperature is maintained at 20 mm Hg for 3 hours. The contents are cooled to 180° C. and then poured into a stainless vat and solidified.

The product is a light yellow glassy solid, having a softening point of 78° C., a phosphorus content of 10.2% and a hydroxyl value of 34.

EXAMPLE 1-3

432 g of the product of Example 1 and 53.6 g of pentaerythritol are charged into the same flask as in Example 1-2 and heated. When the contents are elevated to 140° C., stirring is effected. When heating of the flask is continued, the contents are elevated at a rate of 20° C. per one hour. After elevating to 240° C., the water outlet is connected with a vacuum pump and reaction is advanced at this temperature under reduced pressure of 20 mm Hg for 3 hours. The contents are cooled at 180° C., poured into a stainless vat and solidifed.

The product is a light yellow glassy solid, having a softening point of 99° C., a phosphorus content of 10.15% and a hydroxyl value of 8.

EXAMPLE 1-4

432 g of the product by the process of Example 1 and 66.7 g of dipentaerythritol (Koei Kagaku Kogyo K. K.) are charged into the same flask as in Example 1-2, and a light yellow glassy solid is obtained according to the same procedure as in Example 1-3.

The product has a softening point of 103° C., a phosphorus content of 10.1% and a hydroxyl value of 8.

EXAMPLE 1-5

432 g of the product by the process of Example 1 and 69 g of mannite are charged into the same flask as in Example 1-2. Heating the flask, the contents melt at 140° C., and are stirred. Then the temperature is elevated at a rate of 10° C. per hour, and at 200° C. the water outlet is connected with a vacuum pump to reduce the pressure to 20 mm Hg, where a reaction is conducted for an hour. The contents are poured into a stainless vat and solidified.

The product obtained is a light yellow glassy solid with a slight muddiness, having a softening point of 126° C., a phosphorus content of 9.8% and a hydroxyl value of 87.

EXAMPLE 2

350 g of dipentaerythritol are charged into a three-necked flask of 500 ml in capacity provided with a thermometer, a water outlet and a stirrer. The contents are heated to 240° C. and added 0.1 g of paratoluenesulfonic acid while stirring and maintaining the temperature for three hours.

The product is poured into a stainless vat and solidified. The product has a hydroxyl value of 1253, and is mixture of dipentaerythritol and tetrapentaerythritol.

EXAMPLE 2-2

432 g of the product of Example 1 and 70.4 g of the product of Example 2 are charged into the same flask as in Example 1-2, and reaction is conducted in the same manner as in Example 1-3. The product obtained is a light yellow glassy solid, having a softening point of 105° C., a phosphorus content of 9.3% and a hydroxyl value of 7.

EXAMPLE 3

442.5 g of 6-bromo-9,10-dihydro-9-oxa-10-phosphorphenanthrene-10-oxide and 450 g of ethylene glycol monoethyl ether are charged into a four-necked flask of 1,000 ml in capacity provided with a thermometer, a dropping funnel, a reflux condenser and a stirrer, and heated to 130° C. While stirring, 160 g of ethyl acrylate are added dropwise over five hours and thereafter the contents are heated for a further 10 hours so as to the reflux slightly. The neck of the reflux condenser is replaced with a distillation apparatus, and unreacted ethyl acrylate and ethylene glycol monoethyl ether are removed. At the end of step, volatile components are removed at 180° C. and a reduced pressure of 3 mm Hg.

The product obtained is a light yellow sticky type, having a phosphorus content of 7.8% (calculated 7.85%) and a saponification value of 282 (calculated 283.5), represented by the following structure.

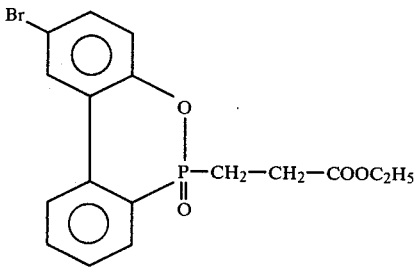

EXAMPLE 3-2

395 g of the product of Example 3, 35.7 g of pentaerythritol, 0.05 g of zinc acetate and 0.02 g of germanium oxide are charged into the same flask as in Example 1-2 and heated to 130° C. Then, stirring is effected and the temperature of the contents is elevated at a rate of 20° C. per hour to 250° C. Thereafter the water outlet is connected with a vacuum pump to reduce the pressure to 20 mm Hg and reaction is effected for a further two hours maintaining the temperature. The contents are cooled to 180° C., poured into a stainless vat, and solidified.

The product obtained is light yellow glassy solid, having a softening point of 126° C., a phosphorus content of 7.2% and a hydroxyl value of 4.5.

EXAMPLE 4

324 g of 9,10-dihydro-9-oxa-10-phosphorphenanthrene-10-oxide are charged into a three-necked flask of 500 ml in capacity provided with a thermometer, a dropping funnel, a reflux condenser and a stirrer, and heated to 140° C. Then, 116 g of trimethylol propane ester of methacrylic acid are added dropwise from the dropping funnel over four hours while stirring the contents. Thereafter the contents are heated to 180° C. and reacted for further four hours. The contents are poured into a stainless vat, cooled and solidified.

The product is a light yellow glassy solid, having a softening point of 68° C. and a phosphorus content of 9.8°.

EXAMPLE 5

446 g of an organophosphorus compound (melting point: 219° C., phosphorus content: 6.96%, bromine content: 35.9%, and acid value: 125) represented by the structure,

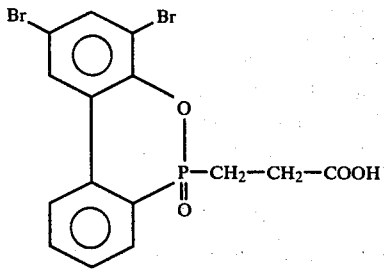

(hereinafter referred to as CECA-BII)

and 35.7 g of pentaerythritol are charged into the same flask as in Example 1-2, and heated to 220° C. At this temperature stirring is effected and reaction is conducted for three hours while removing water.

The water outlet is connected with a vacuum pump to reduce the pressure to 20 mm Hg, and the contents are further heated to 250° C. and reacted for four hours. The contents are cooled to 210° C., and then poured into a stainless vat.

The product is a light yellow glassy solid, having a softening point of 137° C., a phosphorus content of 6.7% and a hydroxyl value of 5.

EXAMPLE 6

446 g of CECA-BII and 44.5 g of dipentaerythritol are charged into the same flask as in Example 1-2. When the temperature of the contents is elevated to 220° C., stirring is started and reaction is effected for two hours. Then the pressure in the flask is reduced to 20 mm Hg, and the contents are heated to 250° C. and reacted for four hours. The contents are cooled to 220° C. and poured into a stainless vat.

The product is a light yellow glassy solid, having a softening point of 140° C., a phosphorus content of 6.6% and a hydroxyl value of 5.

EXAMPLE 7

446 g of CECA-BII and 72.6 g of dipentaerythritol are charged into the same flask as in Example 1-2, and the flask is heated. When the temperature of the contents is elevated to 220° C., stirring is effected. After two hours the pressure in the flask is reduced to 20 mm Hg and reaction is effected for two hours while maintaining the temperature. The contents are poured into a stainless vat and solidified.

The product is a light yellow glassy solid having a softening point of 147° C., a phosphorus content of 6.2% and a hydroxyl value of 81.

EXAMPLE 8

479 g of 2,6,8-trichloro-9,10-dihydro-9-oxa-10-phosphorphenanthrene-10-oxide and 400 g of anisole are charged into the same flask as in Example 1, and the flask is heated When the temperature of the contents is elevated to 150° C., stirring is effected and the heating is adjusted so as to reflux the contents quite slightly. Under this condition 155 g of ethyl acrylate are added dropwise from the dropping funnel over 4 hours. Following the addition of ethyl acrylate, reaction is continued under the same conditions. Then the reflux condenser is replaced with water outlet to remove unreacted ethyl acrylate and anisole used as a solvent. At last volatile components are removed at the temperature of 180° C. and the pressure of 1 mm Hg.

The product is a light yellow glassy solid, having a phosphorus content of 7.3%.

EXAMPLE 8-2

420 g of the product of Example 8 and 85 g of dipentaerythritol are charged into the same flask as in Example 1-2, and the flask is heated. At the temperature of 130° C. the contents are subject to stirring and 0.2 g of sodium methylate is added. The temperature is further elevated at a rate of 20° C. per hour to 180° C. Then the pressure in the flask is reduced to 20 mm Hg and reaction is conducted for an hour while maintaining the temperature. The contents thus obtained are poured into a stainless vat, cooled and solidified.

The product is a light yellow glassy solid with a slight muddiness, having a phosphorus content of 6.8% and a hydroxyl value of 118.

EXAMPLE 9

374 g of 6,8-dibromo-9,10-dihydro-9-oxa-10-phosphorphenanthrene-10-oxide, 45 g of dipentaerythritol and 89 g of crotonic acid are charged into the same flask as in Example 1-2, and the flask is heated. When the temperature of the contents is elevated to 180° C., stirring is effected. At the same time, removing water generated, the temperature is elevated at the rate of 10° C. per hour to 240° C. Then the water outlet is connected with a vacuum pump to reduce the pressure to 20 mm Hg. Reaction is further effected for four hours at this temperature.

After the contents are cooled to 220° C., they are poured into a stainless vat and solidified.

The product is a light brown glassy type, having a softening point of 143° C., a phosphorus content of 6.1% and a hydroxyl value of 7.5.

EXAMPLE 10

Each of the condensation products of the above Examples is blended with thermoplastic resins in Brabender mill. Samples for burning test of 3.2 mm thickness, 12.2 mm wide and 152.4 mm long are obtained by subjecting the blend to compression molding. Rating of a flame retardancy is decided by measuring a burning time of a test sample according to the standard of Underwriter's Laboratories Inc., Subject 94 (hereinafter referred to as UL-94).

1 A: Polystyrene (without flame retardant)
1 B: Polystyrene-Example 5 (20) (Indicated by a composition consisting of 100 parts by weight of polystyrene and 20 parts by weight of the condensation product of Example 5. Such a way of indication is used in the following).
1 C: Polystyrene-Example 9 (18)
2 A: Acrylonitrile-styrene resin (without flame retardant)
2 B: Acrylonitrile-styrene resin-Example 9 (18)
3 A: Acrylonitrile-butadiene-styrene resin (without flame retardant)
3 B: Acrylonitrile-butadiene-styrene resin-Example 5 (20)
4 A: Polyvinyl chloride-plasticizer (50) (without flame retardant)
4 B: Polyvinyl chloride-plasticizer-Example 3-2 (15)
5 A: Bisphenol A-terephthalic acid polycondensate (without flame retardant)

5 B: Bisphenol A-terephthalic acid polycondensate-Example 6 (6)
6 A: Polycarbonate resin (without flame retardant)
6 B: Polycarbonate resin-Example 5 (7)
7 A: Polyphenylene oxide-polystyrene (70) (without flame retardant)
7 B: Polyphenylene oxide-polystyrene (70)-Example 1-3 (15)
7 C: Polyphenylene oxide-polystyrene (70)-Example 1-4 (15)
7 D: Polyphenylene oxide-polystyrene (70)-Example 2-2 (15)
7 E: Polyphenylene oxide-polystyrene (70)-Example 4 (15)
7 F: Polyphenylene oxide-polystyrene (70)-Example 5 (8)
8 A: Polyamide (6-Nylon) (without flame retardant)
8 B: Polyamide-Example 1-5 (20)
8 C: Polyamide-Example 7 (15)
8 D: Polyamide-Example 8-2(15)

The appearance of samples and test results are given in Table 1.

| Run No. | Appearance | Impact*[1] Strength | Rating on Flame*[2] Retardancy |
|---|---|---|---|
| 1 A | Transparent | 1.7 | — |
| 1 B | Slightly turbid | 0.5 | V-1 |
| 1 C | Semitransparent | 0.7 | V-1-V-0 |
| 2 A | Transparent | 3.2 | — |
| 2 B | Semitransparent | 1.1 | V-1-V-0 |
| 3 A | Opaque | 1.7 | — |
| 3 B | " | 0.5 | V-0 |
| 4 A | Transparent | — | SB |
| 4 B | " | — | V-0 |
| 5 A | " | 35 | SB |
| 5 B | " | 9.5 | V-0 |
| 6 A | " | 55 | V-2 |
| 6 B | " | 12.1 | V-0 |
| 7 A | Semitransparent | 13.5 | SB |
| 7 B | " | 6.6 | V-1-V-0 |
| 7 C | " | 7.5 | V-1-V-0 |
| 7 D | " | 7.3 | V-1-V-0 |
| 7 E | " | 8.8 | V-1 |
| 7 F | " | 7.5 | V-0 |
| 8 A | " | 18 | SB |
| 8 B | Opaque | 4.2 | V-2 |
| 8 C | " | 5.6 | V-1-V-0 |
| 8 D | " | 7.0 | V-1 |

*[1]Indicated by Izod impact strength with ⅛ inch notch in kg . cm/cm².
*[2]Indicated by the magnitude of flame retardancy. V-0 > V-1 > V-2 > SB

EXAMPLE 11

300 g of polypropylene glycol (average molecular weight 600) are blended with 400 g of the condensation product of Example 1-5 and then 140 g of toluylene diisocyanate are blended together. A test sample is prepared by casting the blend to 3.2 mm thickness and curing at 100° C. for 10 hours.

A burning test is conducted according to the method of Example 10 and the flame retardancy is rated V-O.

EXAMPLE 12

500 g of Epikote 832 (trade name by Shell Int. Chemicals Corp.) are blended with 100 g of the condensation product of Example 8 and then, 100 g of 4,4'-diaminodiphenyl ether are blended together. A test sample is prepared by casting the blend to 3.2 mm thickness and curing at 50° C. for 10 hours.

A burning test is conducted according to the method of Example 10 and the flame retardancy is rated V-O.

EXAMPLE 13

100 g of a resol type phenol-formaldehyde polycondensate in form of powders are pulverized and blended with 30 g of the condensation product of Example 1-2. A test sample is prepared by subjecting the blend to compression molding at 160° C. and 100 kg/cm² for one hour to form 3.2 mm thickness.

A burning test is conducted according to the method of Example 10 and the flame retardancy is rated V-O.

EXAMPLE 14

100 g of trimethylol melamine are mixed with 7 g of the condensation product of Example 7 and pulverized together.

A test sample is prepared by subjecting the blend to compression molding at 140° C. and 100 kg/cm² for 20 minutes to form 3.2 mm thickness.

A burning test is conducted according to the method of Example 10 and the flame retardancy is rated V-O.

EXAMPLE 15

20 g of the condensation product of Example 5 are dissolved in 50 g of styrene and 100 g of an unsaturated polyester (synthesized from neopentyl glycol, phthalic anhydride and maleic anhydride) and 0.5 g of lauroyl peroxide are added thereto.

A test sample is prepared by casting the blend to 3.2 mm thickness and curing at 82° C. for 20 minutes.

A burning test is conducted according to the method of Example 10 and the flame retardancy is rated V-O.

Similar results to those reported in Examples 10 through 15 are obtained with the other resins with which the flame retardant condensates of the present invention are noted as useful, as well as when employing the other flame retardants generically disclosed.

What is claimed is:

1. A flame retardant comprising phosphorus-containing condensation products of an organophosphorus compound represented by Formula I, $$\text{Formula I}$$

wherein X, Y and Z each is hydrogen or halogen, $R_1$ and $R_2$ each is hydrogen or methyl and $R_3$ is hydrogen or an alkyl group with a polyhydric alcohol having at least three alcoholic hydroxyl groups selected from the class consisting of glycerine, polyglycerines, trimethylol ethane, trimethylol propane, pentaerythritol, dipentaerythritol, tripentaerythritol, tetrapentaerythritol, mannite and sorbite, where said condensation products have a phosphorus content of 6.0 to 10.7% by weight and a softening point of 55°–155° C.

2. A flame retardant phosphorus-containing condensation product wherein said condensation product is obtained by an addition reaction between acrylic, methacrylic or crotonic acid esters of a polyhydric alcohol having at least three alcoholic hydroxyl groups selected from the class consisting of glycerine, polyglycerines, trimethylol ethane, trimethylol propane, pentaerythritol, dipentaerythritol, tripentaerythritol, tetrapentaerythritol, mannite and sorbite, and an organophosphorus compound of Formula II,

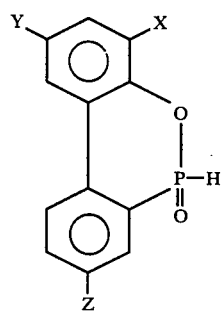

II wherein X, Y and Z each is hydrogen or halogen.

3. The flame retardant of claim 1 wherein said condensation products are a reaction product in a ratio of 35–130 of the Formula I compound relative to 100 of number of hydroxyl groups in the polyhydric alcohol.

4. A flame retardant resin composition comprising 100 parts by weight of a thermoplastic resin and 3 to 50 parts by weight of phosphorus-containing condensation products of an organophosphorus compound represented by Formula I,

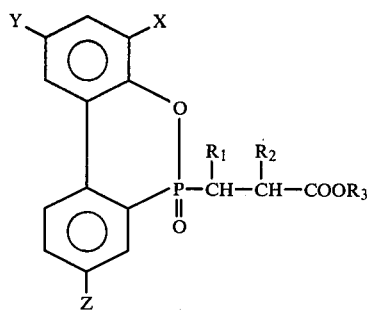

I wherein X, Y and Z each is hydrogen or halogen, $R_1$ and $R_2$ each is hydrogen or methyl and $R_3$ is hydrogen or an alkyl group with a polyhydric alcohol having at least three alcoholic hydroxyl groups, where said condensation products have a phosphorus content of 6.0 to 10.7% by weight and a softening point of 55°–155° C.

5. The flame retardant resin composition of claim 4 wherein said thermoplastic resin is selected from the group consisting of polystyrene, acrylonitrile-styrene resins, acrylonitrile-butadiene-styrene resins, polyvinyl chloride, polyterephthalate resins, polycarbonate resins, polyphenylene oxide resins and polyamide resins.

6. A flame retardant resin composition comprising 100 parts by weight of a thermosetting resin and 3 to 50 parts by weight of phosphorus-containing condensation products of an organophosphorus compound represented by Formula I,

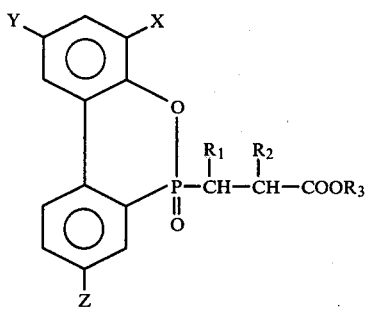

I wherein X, Y and Z each is hydrogen or halogen, $R_1$ and $R_2$ each is hydrogen or methyl and $R_3$ is hydrogen or an alkyl group with a polyhydric alcohol having at least three alcoholic hydroxyl groups, where said condensation products have a phosphorus content of 6.0 to 10.7% by weight and a softening point of 55°–155° C.

* * * * *

UNITED STATES PATENT AND TRADEMARK OFFICE
CERTIFICATE OF CORRECTION

PATENT NO. : 4,280,951
DATED : July 28, 1981
INVENTOR(S) : Toranosuke Saito et al It is certified that error appears in the above—identified patent and that said Letters Patent is hereby corrected as shown below:

Column 2, line 66 change "10-dihydro-B 9-oxa," to --10-dihydro-9-oxa,--

Column 4, lines 63-64 change "the number of hydroxyl groups of the Formula I" to --the number of the Formula I--

Column 6, line 63 change "(1.5 x 7/8 x 1.2 moles)" to --(1.5 x 1/3 x 1.2 moles)--

Column 9, line 60 after "heated" insert --.--

Signed and Sealed this

Thirtieth Day of March 1982

[SEAL]

Attest:

Attesting Officer

GERALD J. MOSSINGHOFF
Commissioner of Patents and Trademarks